United States Patent
You et al.

(10) Patent No.: US 6,521,268 B2
(45) Date of Patent: Feb. 18, 2003

(54) **ANTIBACTERIAL AND ANTI-INFLAMMATORY COMPOSITIONS WITH *INULA HELENIUM L.* EXTRACT AND WATER SOLUBLE CHITOSAN**

(75) Inventors: Hyung Ja You, Kyungki-do (KR); Sang Bong Seo, Kyungki-do (KR); Chan Seok Seo, Kyungki-do (KR)

(73) Assignee: Jakwang Co., Ltd., Ansung (KR)

( * ) Notice: Subject to any disclaimer, the term of this patent is extended or adjusted under 35 U.S.C. 154(b) by 0 days.

(21) Appl. No.: 09/866,738

(22) Filed: May 30, 2001

(65) Prior Publication Data

US 2002/0155175 A1 Oct. 24, 2002

(30) Foreign Application Priority Data

Feb. 8, 2001 (KR) .............................. 01-6226

(51) Int. Cl.[7] .......................... A61K 35/78; A61K 6/00; A61K 47/00; A61K 35/64; A23K 1/17
(52) U.S. Cl. ................. 424/725; 424/401; 424/439; 424/442; 424/538
(58) Field of Search ................ 424/725, 401, 424/439, 442, 538

(56) References Cited

U.S. PATENT DOCUMENTS 5,178,865 A * 1/1993 Ho et al.
5,730,876 A    3/1998 You et al.
5,980,912 A * 11/1999 Podolski et al.

FOREIGN PATENT DOCUMENTS

JP    20002561    * 9/2000

OTHER PUBLICATIONS

1993–234307; Jul. 1992, Derwent, Dolgikh.*

2000–472841; Jul. 1999, Derwent, Kim et al.*

Jeong et al, "International Journal of Immunopharmacology" 22, 2000, 923–933.

* cited by examiner

*Primary Examiner*—Christopher R. Tate
*Assistant Examiner*—Randall Winston
(74) *Attorney, Agent, or Firm*—Finnegan, Henderson, Farabow, Garrett & Dunner, L.L.P.

(57) ABSTRACT

The present invention relates to a natural cell control carrier, more specifically to a natural cell control carrier containing water-soluble chitosan (HFP) and elecampane (Inula Helenium L.) extract, which solves problems of conventional synthesized antibacterial agents and provides various superior properties, improved antibacterial activity and anti-inflammatory effect with a broad antibacterial spectrum, so that it can be used for food, cosmetics and medicine.

6 Claims, No Drawings

ANTIBACTERIAL AND ANTI-INFLAMMATORY COMPOSITIONS WITH *INULA HELENIUM L.* EXTRACT AND WATER SOLUBLE CHITOSAN

BACKGROUND OF THE INVENTION

Field of the Invention

The present invention relates to a natural cell control carrier, more specifically to a natural cell control carrier comprising water-soluble chitosan (HFP) and elecampane (Inula Helenium L.) extract, which solves problems of conventional synthesized antibacterial agents and provides various superior properties, improved antibacterial effect and anti-inflammatory effect with a broad antibacterial spectrum, so that it can be used for food, cosmetics and medicine.

Generally, microorganisms that contaminate food, cosmetics and medicine may be classified into bacteria and fungi. Bacteria can be classified into Gram-positive bacteria and Gram-negative bacteria; and fungi can be classified into yeast and mold. These microorganisms are known to flourish in wet environments. Especially, microorganisms flourish in environments with high water activity (Aw) like cosmetics. If microorganisms flourish in food and cosmetics, gas may be generated due to the decomposition of carbohydrates; the food and cosmetics may become rancid due to the generation of fatty acid or ketone residue from oil and fat compounds; and stench may be generated due to the decomposition of proteins. Antibacterial agents are used to prevent from deterioration of products like cosmetics caused by the contamination and multiplication of microorganisms. The common antibacterial agents used in food, cosmetics and medicine are methyl p-hydroxybenzoate, propyl p-hydroxybenzoate, imidazolinyl urea, citric acid, propylene glycol and phenoxyethanol. These antibacterial agents may be mixed each other in an appropriate content or other substances reinforcing the antibacterial system are arbitrarily incorporated to provide better antibacterial activity.

However, synthesized antibacterial agents have the problems such as increased tolerance, side effect, toxicity, carcinogenicity and the generation of unidentified substances. Therefore, restriction of items and limitation of usage about synthesized antibacterial agents are becoming strict and the purchasing power is declining due to the restriction of consumption and decline of warning attractiveness toward customers. Also, a small amount of synthesized antibacterial agent used in medicine, food and cosmetics may cause skin-related side effects like contact dermatitis or allergy, due to irritation and toxicity to skin.

Accordingly, the antibacterial agent used in medicine, food and cosmetics should have antibacterial activity but low irritation to skin and no toxicity and tolerance. The present invention relates to a natural cell control carrier that satisfies this requirement, which comprises water-soluble chitosan (HFP) and elecampane extract (Inula Helenium L.).

Although the antibacterial activity of chitosan is widely known, its mechanism is hardly understood. It is only presumed that the positive charge in the amine group of chitosan and the negative charge in the cell wall of the microorganism interact to prevent the growth of the microorganism. The inventors have verified the superior cell activity, like strong NO-generation function of cell, prevention against genetic mutation, prevention against chromosomal mutation, cell regeneration competence and cell regulation property, stability and nontoxicity of water-soluble chitosan (HFP) [*International Journal of Immunopharmacology*, 22. 2000, 923–933; U.S. Pat. No. 5,730,876]. The experiments performed by the inventors and others show that said water-soluble chitosan (HFP) has a strong antibacterial activity against bacteria and yeast, but no or decreased antibacterial activity against mold.

SUMMARY OF THE INVENTION

The inventors have studied to develop a natural cell control carrier with superior properties and broad antibacterial spectrum using water-soluble chitosan (HFP) in antibacterial agent. The inventors realized that if water-soluble chitosan (HFP) is used together with elecampane extract (Inula Helenium L.), it provides superior antibacterial activity against mold as well as bacteria and yeast and an anti-inflammatory effect. Therefore, a new natural cell control carrier was developed. The test result showed that the natural cell control carrier obtained by combining water-soluble chitosan (HFP) and elecampane extract (Inula Helenium L.) provides excellent antibacterial activity against bacteria, yeast and mold, 30%–60% lower of skin irritation evaluated by patch test than that of synthesized antiseptic and superior anti-inflammatory effect.

Accordingly, an object of the present invention is to provide a natural cell control carrier with broad antibacterial spectrum and anti-inflammatory effect and with little irritation to skin.

DETAILED DESCRIPTION OF THE INVENTION

The present invention is characterized by a natural cell control carrier comprising water-soluble chitosan (HFP) and elecampane extract (Inula Helenium L.).

The present invention includes an antibacterial agent that contains a natural cell control carrier comprising water-soluble chitosan (HFP) and elecampane extract (Inula Helenium L.).

The present invention also includes an anti-inflammatory agent that contains a natural cell control carrier comprising water-soluble chitosan (HFP) and elecampane (Inula Helenium L.) extract as well.

Hereunder is given a more detailed description of the present invention.

The antibacterial mechanism of the natural cell control carrier according to the present invention originates from the positive (+) charge of the constituents in the water-containing system (phase). Teichoic acid, a constituent of bacteria's cell wall, regulates the expansion of the cell wall and has a negative charge. Therefore the surface of the cell wall carries a negative (−) charge because of teichoic acid. Accordingly the natural cell control carrier of the present invention, which carries a positive (+) charge, forms a strong ionic bond to the bacteria's cell wall with a negative (−) charge, and strongly prevents the activity of bacteria and their growth. The bacteria are severely damaged by the strong ionic bond and transfer of drug and lose their activity rapidly.

The natural cell control carrier of the present invention provides an effective anti-inflammatory effect as well as said antibacterial activity. Inflammation is the reaction of a living tissue against damage. Inflammation is a defensive mechanism to return to the normal state by localizing the damage when a biologic tissue is damaged due to some reason. Reactions of blood vessel, nerve, body fluid and cell are related with inflammation. For the causes of inflammation, there are biological cause (bacteria), physical cause (injury), chemical cause (endogenous or exogenous chemical substances) and immunological cause. The inflammation reactions are characterized by the change in blood vessel, exudation of liquid and leukocyte invasion, and their typical symptoms are flare, swelling, fever and pain. The natural cell control carrier of the present invention is particularly superior in the restoration of leukocyte invasion.

Hereunder is given a specific description about the constitution of the natural cell control carrier of the present invention.

The water-soluble chitosan having a molecular weight of from 100,000 to 300,000 used in the present invention has been prepared based on the method disclosed in U.S. Pat. No. 5,730,876. Based upon its water-soluble characteristic the prepared chitosan is bound to immunoprotein, so that it recognizes cell and amino acid as a cell controller modular and the tRNA stimulates the cell to generate an indirect effect. This water-soluble chitosan (HFP) has superior cell activity, such as activating NO-generation in the cell and preventing of genetic mutation, cell regeneration competence and cell regulation property, superior stability and proven nontoxicity [HFP™, Ja Kwang's product; *International Journal of Immunopharmacology* 22. 2000, 923–933].

Another constituent of the natural cell control carrier of the present invention is elecampane extract. Although the effective constituent of elecampane (Inula Helenium L.) is not known yet, its essential oil is widely used in food and medicine because it has antiseptic effect, anti-inflammatory effect and vermicidal effect. In the rhizome and root of elecampane (Inula Helenium L.), there is 1–5% of essential oil. The crystal of this essential oil is called 'helenin', which is a mixture of selinane-type sesqiterpene lactone. The main components of this mixture are alantolactone ($C_{15}H_{20}O_2$), isoalantolactone ($C_{15}H_{20}O_2$), dihydroalantolactone ($C_{15}H_{22}O_2$), alantolic acid, etc. Besides helenin, damiladienyl acetate ($C_{32}H_{52}O_2$), a triterpene alcohol, a small amount of alantol ($C_{15}H_{23}O_2$) and proazulene are included in the essential oil. The root contains inulin (up to 44%), pseudoinulin, inulenin, saponin, bitterly tasting materials, pigments and a trace of alkaloid.

In the present invention, elecampane extract obtained from the following extraction process is used as an effective constituent. After slicing the root of elecampane (Inula Helenium L.) and precipitating it in 50–80% ethanol for 3–10 days, it is filtered firstly. After maturating the residue solution for 3–7 days at low temperature (−4° C.), the undissolved residue is precipitated and filtered secondly. This filtered elecampane extract solution is dried in a rotary evaporator and a freeze dryer to obtain solid elecampane extract.

After re-freeze-drying a solution comprising said soluble chitosan (HEP) and elecampane extract (Inula Helenium L.), a physical induction process using biological separation method like dialysis is performed to obtain the natural cell control carrier of the present invention.

The composition of water-soluble chitosan (HFP) and elecampane extract (Inula Helenium L.) comprising the natural cell control carrier of the present invention is determined base on each minimum inhibition concentration (MIC) result.

| Composition (wt%) | | Minimum Inhibition Concentration (MIC; mg/mL) | | | | |
|---|---|---|---|---|---|---|
| Water-soluble chitosan (HFP) | Elecampane extract | *Staphylococcus aureus* | *Escherichia coli* | *Pseudomonas aeruginosa* | *Candida albicans* | *Aspergillus niger* |
| 0 | 100 | 5.0 | >60.0 | 40.0 | >70.0 | 1.0 |
| 30 | 70 | 2.1 | 2.6 | 6.0 | 1.5 | 0.9 |
| 50 | 50 | 1.3 | 2.8 | 7.0 | 1.6 | 2.1 |
| 70 | 30 | 1.2 | 2.2 | 2.1 | 1.3 | 0.7 |
| 100 | 0 | 1.5 | 2.5 | 2.5 | 1.5 | >5.0 |

The natural cell control carrier of the present invention comprises 0.01–99.99 wt % of water-soluble chitosan (HFP) and 0.01–99.99 wt % of elecampane extract, preferably 50.00–90.00 wt % of water-soluble chitosan (HFP) and 10.00–50.00 wt % of elecampane extract. Differently, a natural antibacterial agent may be dissolved in pure water to 1–30% (w/v) concentration and freeze-dried again in order to commercialize the natural cell control carrier according to the present invention. As can be seen in the above table, though each of chitosan (HFP) and elecampane extract has antibacterial effect of its own, the natural cell control carrier with specific composition has increased antibacterial effect due to the continuity, transferability and interdependence of chitosan (HFP). The effect is maximized at critical range by complementing each other.

The antibacterial activity test result of the natural cell control carrier of the present invention showed very superior antibacterial effect against bacteria, yeast and mold. Also, it showed 30%–60% lower skin irritation than conventional synthesized antibacterial agent, and superior anti-inflammatory effect.

Hereunder is given a more detailed description of the present invention using examples. However, it should not be construed as limiting the scope of the present invention.

PREPARING EXAMPLE 1

Preparing of Water-Soluble Chitosan [Cf. U.S. Pat. No. 5,730,876]

By an abscission reaction of variable ultrasonic process in the range of 30–70 kHz at 25–40° C. in the lysozyme and chitosanase enzyme solution, a small-molecular-weight part was removed through a reverse-direction membrane separation process. Water-soluble chitosan with relatively large molecular weight was obtained by performing filtering and free drying repeatedly. The molecular weight range of oligosaccharide of the obtained water-soluble chitosan was 100,000–300,000. Immunoprotein was nanocoated (size: 50 nm) to obtain a cell carrier form. Water-soluble chitosan of this type is being marketed as JaKwang's HFP™.

PREPARING EXAMPLE 2

Preparation of Elecampane Extract

After slicing the root of elecampane (Inula Helenium L.), it was precipitated in 70% ethanol for 5 days. After filtering this solution, the remaining solution was maturated for 5 days at low temperature (−4° C.) for the undissolved material to precipitate, and was filtered again. The filtered elecampane extract solution was dried in a rotary evaporator and a freeze dryer to obtain a solid elecampane extract.

EXAMPLE 1

Comparison of Antibacterial Activity

The following experiments were performed to compare the antibacterial activity of each cell carrier comprising water-soluble chitosan (HFP), elecampane (Inula Helenium L.) extract and water-soluble chitosan-elecampane extract.

After selecting 5 typical microbes recommended by the CTFA Microbiological Guideline, the minimum inhibition concentration (MIC) of each microbial strain was measured with the standard plate count method. The minimum inhibition concentration (MIC) was determined by streaking the test microbes in agar plate including each cell carrier comprising water-soluble chitosan (HFP), elecampane extract (Inula Helenium L.) and water-soluble chitosan-elecampane extract with different concentration, culturing them for 3 days and identifying the growth of the microbes.

1. Tested Microbes

Gram-positive bacterium: *Staphylococcus aureus*, ATCC 6538P

Gram-negative intestinal bacterium: *Escherichia coli*, ATCC 8739

Gram-negative bacterium: *Pseudomonas aeruginosa*, ATCC 9027

Yeast: *Candida albicans*, ATCC 10231

Mold: *Aspergillus niger*, ATCC 9642

2. Media

Nutrient agar medium and potato dextrose agar medium

TABLE 1

Minimum Inhibition Concentration (MIC; mg/mL)

| Tested microbes | Chitosan[1] | Chitosan[2] | Elecampane extract | Chitosan[2]-elecampane extract (3:1) |
|---|---|---|---|---|
| *Staphylococcus aureus* | >55 | 1.5 | 5.0 | 10 |
| *Escherichia coli* | >50 | 2.5 | >60.0 | 2.0 |
| *Pseudomonas aeruginosa* | >60 | 2.5 | 40.0 | 2.0 |
| *Candida albicans* | >50 | 1.5 | >70.0 | 1.0 |
| *Aspergillus niger* | >70 | >5.0 | 1.0 | 0.5 |

[1]Chitosan: AMW. ≧20,000
[2]Chitosan: AMW. ≦200,000 (Ja Kwang's HFP ™)

As shown in Table 1, the antibacterial activity of water-soluble chitosan (HFP) was reinforced by elecampane (Inula Helenium L.) extract. Since the antibacterial constituent should have antibacterial activity against various microbial strains to be used in cosmetics, etc., antibacterial activity against the typical microbes represented in Table 1 is mandatory. Table 1 shows that even if water-soluble chitosan (HFP) and elecampane (Inula Helenium L.) may have deficiency when used alone, they form an antibacterial agent with superior quality when used together. The superior antibacterial activity of the cell carrier comprising water-soluble chitosan-elecampane extract according to the present invention originates from the inherent characteristics of water-soluble chitosan (HFP). Since water-soluble chitosan (HFP) has considerably superior quality-improving property and continuation property, it improves the properties of other materials used together like elecampane extract. The natural cell control carrier of the present invention provides antibacterial action comparable to that of conventional synthesized antibacterial agents as to replace them.

EXAMPLE 2

Test of Antibacterial Activity in Skin Lotion Form

Antibacterial activity against *Staphylococcus aureus* (ATCC 6538P), *Escherichia coli* (ATCC 8739), *Pseudomonas aeruginosa* (ATCC 9027), *Candida albicans* (ATCC 10231) and *Aspergillus niger* (ATCC 9642) microbial strains were tested for the skin lotions 1–4 with composition shown in the following Table 2. The test result is shown in Tables 2a–2e.

TABLE 2

| Components | Skin Lotion 1 | Skin Lotion 2 | Skin Lotion 3 | Skin Lotion 4 |
|---|---|---|---|---|
| DL-panthenol | 0.20 | 0.20 | 0.20 | 0.20 |
| Betaine | 4.00 | 4.00 | 4.00 | 4.00 |
| Ethoxydiglycol | 0.50 | 0.50 | 0.50 | 0.50 |
| Methyl gluces-20 | 0.80 | 0.80 | 0.80 | 0.80 |
| PEG/PPG (17/6) copolymer | 1.00 | 1.00 | 1.00 | 1.00 |
| Glycerin | 1.50 | 1.50 | 1.50 | 1.50 |
| Water-soluble chitosan/elecampane extract (3:1) | 5.00 | 10.00 | — | — |
| Ethanol | 7.00 | 7.00 | 7.00 | 7.00 |
| Methyl p-benzoate | — | — | 0.1 | — |
| PPG-26 betes-26/PEG-40 hydrogenated caster oil | 0.20 | 0.20 | 0.20 | 0.20 |
| Lactic acid (10%) | — | — | 0.17 | 0.17 |
| Compound fragrance | Proper quantity | Proper quantity | Proper quantity | Proper quantity |
| Pure water | Proper quantity | Proper quantity | Proper quantity | Proper quantity |

TABLE 2a

**Antibacterial Activity against *Staphylococcus aureus***

| Items | Immediately after inoculation | After 1 hr | After 2 hr | After 4 hr | After 8 hr | After 24 hr |
|---|---|---|---|---|---|---|
| Skin lotion 1 | 7.00E+06 | <1.00E+01 | <1.00E+01 | <1.00E+01 | <1.00E+01 | <1.00E+01 |
| Skin lotion 2 | 7.00E+06 | <1.00E+01 | <1.00E+01 | <1.00E+01 | <1.00E+01 | <1.00E+01 |
| Skin lotion 3 | 7.00E+06 | <1.00E+01 | <1.00E+01 | <1.00E+01 | <1.00E+01 | <1.00E+01 |
| Skin lotion 4 | 7.00E+06 | <1.00E+01 | <1.00E+01 | <1.00E+01 | <1.00E+01 | <1.00E+01 |

TABLE 2b

**Antibacterial Activity against *Escherichia coli***

| Items | Immediately after inoculation | After 1 day | After 2 days | After 4 days | After 8 days | After 24 days |
|---|---|---|---|---|---|---|
| Skin lotion 1 | 6.9E+06 | <1.00E+01 | <1.00E+01 | <1.00E+01 | <1.00E+01 | <1.00E+01 |
| Skin lotion 2 | 6.9E+06 | <1.00E+01 | <1.00E+01 | <1.00E+01 | <1.00E+01 | <1.00E+01 |
| Skin lotion 3 | 6.9E+06 | <1.00E+01 | <1.00E+01 | <1.00E+01 | <1.00E+01 | <1.00E+01 |
| Skin lotion 4 | 6.9E+06 | <1.00E+01 | <1.00E+01 | <1.00E+01 | <1.00E+01 | <1.00E+01 |

TABLE 2c

**Antibacterial Activity against *Pseudomonas aeruginosa***

| Items | Immediately after inoculation | After 1 hr | After 3 hr | After 5 hr | After 7 hr | After 14 hr |
|---|---|---|---|---|---|---|
| Skin lotion 1 | 2.66E+05 | 7.25E+04 | 3.0E+01 | <1.00E+01 | <1.00E+01 | <1.00E+01 |
| Skin lotion 2 | 2.66E+05 | 4.65E+04 | <1.00E+01 | <1.00E+01 | <1.00E+01 | <1.00E+01 |
| Skin lotion 3 | 2.66E+05 | 4.00E+04 | 1.00E+02 | <1.00E+01 | <1.00E+01 | <1.00E+01 |
| Skin lotion 4 | 2.66E+05 | 7.15E+04 | 9.00E+02 | <1.00E+01 | <1.00E+01 | <1.00E+01 |

TABLE 2d

**Antibacterial Activity against *Candida albicans***

| Items | Immediately after inoculation | After 1 day | After 3 days | After 5 days | After 7 days | After 14 days |
|---|---|---|---|---|---|---|
| Skin lotion 1 | 3.20E+06 | 6.00E+03 | 4.00E+02 | <1.00E+02 | <1.00E+01 | <1.00E+01 |
| Skin lotion 2 | 3.20E+06 | 6.00E+03 | 4.50E+02 | <1.00E+02 | <1.00E+01 | <1.00E+01 |
| Skin lotion 3 | 3.20E+06 | 8.00E+03 | <1.00E+02 | <1.00E+01 | <1.00E+01 | <1.00E+01 |
| Skin lotion 4 | 3.20E+06 | 7.00E+03 | 9.00E+02 | <1.00E+02 | <1.00E+01 | <1.00E+01 |

TABLE 2e

**Antibacterial Activity against *Aspergillus niger***

| Items | Immediately after inoculation | After 1 day | After 3 days | After 5 days | After 7 days |
|---|---|---|---|---|---|
| Skin lotion 1 | 1.19E+07 | <1.0E+04 | <1.00E+01 | <1.00E+01 | <1.00E+01 |
| Skin lotion 2 | 1.19E+07 | <1.0E+04 | <1.00E+01 | <1.00E+01 | <1.00E+01 |
| Skin lotion 3 | 1.19E+07 | <1.0E+04 | <1.00E+01 | <1.00E+01 | <1.00E+01 |
| Skin lotion 4 | 1.19E+07 | <1.0E+04 | <1.00E+01 | <1.00E+01 | <1.00E+01 |

From Tables 2a–2e, the antibacterial activity of the skin lotions containing natural cell control carrier of the present invention is similar to that of self-prepared ethanol. However, the antibacterial activity of the natural cell control carrier comprising water-soluble chitosan and elecampane extract according to the present invention against yeast and mold is superior to that of conventional synthesized antibacterial agents, such as methyl p-hydroxybenzoate, propyl p-hydroxybenzoate, imidazolinyl urea, citric acid, propylene glycol and phenoxyethanol.

Another reason why the natural cell control carrier of the present invention provides antibacterial activity superior to that of conventional synthesized antibacterial agents originates from the positive (+) charge in water-containing system (phase). That is, the natural cell control carrier with a positive (+) charge forms a strong ionic bond with the bacteria's cell wall negative (−) charge to give a stronger antibacterial activity.

EXAMPLE 3

Test of Antibacterial Activity in Milk Lotion Form

Antibacterial activity against *Staphylococcus aureus* (ATCC 6538P), *Escherichia coli* (ATCC 8739), *Pseudomonas aeruginosa* (ATCC 9027), *Candida albicans* (ATCC 10231) and *Aspergillus niger* (ATCC 9642) microbial strains were tested for the milk lotions 1–4 with composition shown in the following Table 3. The test result is shown in Tables 3a–3e.

TABLE 3

| Components | Milk Lotion 1 | Milk Lotion 2 | Milk Lotion 3 | Milk Lotion 4 |
| --- | --- | --- | --- | --- |
| Glycerin | 4.00 | 4.00 | 4.00 | 4.00 |
| Disoclium EDTA | 0.02 | 0.02 | 0.02 | 0.02 |
| Methyl p-benzoate | — | — | 0.20 | — |
| Polyglyceryl 3-methyl glucose distearate glucose distearate | 1.55 | 1.55 | 1.55 | 1.55 |
| Glyceryl stearate/PEG-100 stearate | 0.50 | 0.50 | 0.50 | 0.50 |
| Glyceryl stearate | 0.50 | 0.50 | 0.50 | 0.50 |
| Cetearyl alcohol | 0.40 | 0.40 | 0.40 | 0.40 |
| Cholesteryl/behenyl/octyldodecyl lauroyl glutamate | 0.40 | 0.40 | 0.40 | 0.40 |
| Hydrogenated decyl olivate | 0.60 | 0.60 | 0.60 | 0.60 |
| Caprylic/capryic triglyceride | 4.00 | 4.00 | 4.00 | 4.00 |
| Squalane | 3.00 | 3.00 | 3.00 | 3.00 |
| Ethoxy diglycol olate | 2.00 | 2.00 | 2.00 | 2.00 |
| Mido formseed oil | 2.70 | 2.70 | 2.70 | 2.70 |
| Dimethicone | 0.50 | 0.50 | 0.50 | 0.50 |
| Cyclomethicone | 1.50 | 1.50 | 1.50 | 1.50 |
| Imidazolmyl urea | — | — | 0.30 | — |
| Polyacrylamide/C13–14 isoparaffin/laurece-7 | 0.60 | 0.60 | 0.60 | 0.60 |
| Water-soluble chitosan/elecampane Extract (3:1) | 5.00 | 10.00 | — | — |
| Citric acid (10%) | — | — | 0.20 | 0.20 |
| Potassium hydroxide (10%) | 0.50 | 0.50 | — | — |
| Compound fragrance | Proper quantity | Proper quantity | Proper quantity | Proper quantity |
| Pure water | Proper quantity | Proper quantity | Proper quantity | Proper quantity |

TABLE 3a

Antibacterial Activity against *Staphylococcus aureus*

| Items | Immediately after inoculation | After 1 hr | After 2 hr | After 4 hr | After 8 hr | After 24 hr |
| --- | --- | --- | --- | --- | --- | --- |
| Milk lotion 1 | 7.00E+06 | 7.85E+04 | 1.04E+05 | 4.42E+04 | 7.88E+04 | 3.69E+04 |
| Milk lotion 2 | 7.00E+06 | <1.00E+03 | <1.00E+02 | <1.00E+01 | <1.00E+01 | <1.00E+01 |
| Milk lotion 3 | 7.00E+06 | 5.89E+06 | 4.54E+06 | 9.19E+05 | 7.35E+05 | 4.24E+03 |
| Milk lotion 4 | 7.00E+06 | 7.03E+06 | 6.52E+06 | 2.04E+06 | 1.05E+06 | 1.78E+06 |

TABLE 3b

Antibacterial Activity against *Escherichia coil*

| Items | Immediately after inoculation | After 1 day | After 3 days | After 5 days | After 7 days |
| --- | --- | --- | --- | --- | --- |
| Milk lotion 1 | 1.19E+07 | 1.50E+04 | 4.00E+03 | 9.64E+04 | 8.72E+05 |
| Milk lotion 2 | 1.19E+07 | 1.51E+04 | 1.02E+04 | 4.15E+03 | 1.40E+04 |
| Milk lotion 3 | 1.19E+07 | 2.50E+04 | 5.00E+02 | <1.00E+01 | <1.00E+01 |
| Milk lotion 4 | 1.19E+07 | 3.50E+06 | 1.90E+06 | 9.00E+05 | 1.07E+06 |

TABLE 3c

Antibacterial Activity against *Pseudomonas aeruginosa*

| Items | Immediately after inoculation | After 1 hr | After 2 hr | After 4 hr | After 8 hr | After 24 hr |
|---|---|---|---|---|---|---|
| Milk lotion 1 | 6.90E+06 | 3.74E+04 | 2.89E+04 | 2.14E+04 | 1.75E+02 | <1.00E+01 |
| Milk lotion 2 | 6.90E+06 | <1.00E+01 | <1.00E+01 | <1.00E+01 | <1.00E+01 | <1.00E+01 |
| Milk lotion 3 | 6.90E+06 | 2.85E+02 | <1.00E+01 | <1.00E+01 | <1.00E+01 | <1.00E+01 |
| Milk lotion 4 | 6.90E+06 | 1.68E+05 | 1.70E+05 | 3.57E+04 | 2.70E+04 | 3.29E+04 |

TABLE 3d

Antibacterial Activity against *Candida albicans*

| Items | Immediately after inoculation | After 1 day | After 3 days | After 5 days | After 7 days | After 14 days |
|---|---|---|---|---|---|---|
| Milk lotion 1 | 2.66E+05 | 2.10E+04 | 4.55E+02 | <1.00E+02 | <1.00E+01 | <1.00E+01 |
| Milk lotion 2 | 2.66E+05 | 1.05E+04 | 2.45E+02 | <1.00E+02 | <1.00E+01 | <1.00E+01 |
| Milk lotion 3 | 2.66E+05 | 1.15E+05 | 6.00E+02 | 5.10E+02 | 4.40E+02 | 3.75E+02 |
| Milk lotion 4 | 2.66E+05 | 3.61E+05 | 1.34E+06 | 2.32E+05 | 1.54E+06 | 2.30E+06 |

TABLE 3e

Antibacterial Activity against *Aspergillus niger*

| Items | Immediately after inoculation | After 1 day | After 3 days | After 5 days | After 7 days | After 14 days |
|---|---|---|---|---|---|---|
| Milk lotion 1 | 3.20E+06 | 1.00E+03 | 1.45E+03 | 6.45E+02 | 3.40E+02 | 1.00E+02 |
| Milk lotion 2 | 3.20E+06 | 1.50E+03 | 8.00E+02 | 4.45E+02 | 3.15E+02 | 7.50E+01 |
| Milk lotion 3 | 3.20E+06 | 1.00E+03 | 1.00E+02 | 7.50E+01 | 2.00E+01 | <1.00E+01 |
| Milk lotion 4 | 3.20E+06 | 1.25E+04 | 7.70E+03 | 4.75E+03 | 3.40E+03 | 1.70E+03 |

As shown in Tables 3a–3e, though the antibacterial activity of milk lotion 1 containing a small amount of the natural antibacterial agent of the present invention is slightly lower than that of milk lotion 3 (containing synthesized antiseptic), milk lotion 2 which contains an effective amount of the natural cell control carrier of the present invention has comparable antibacterial activity to that of milk lotion 3 for all the five microbes. Moreover, for *Staphylococcus aureus* (Table 3a), *Pseudomonas aeruginosa* (Table 3c) and *Candida albicans* (Table 3d), milk lotion 2 containing the natural antibacterial agent of the present invention provided superior antibacterial activity. Also, the antibacterial activity against *Aspergillus niger*, which is a weakness of chitosan, is maintained sufficiently as can be seen in Table 3e. Therefore, the natural cell control carrier comprising water-soluble chitosan-elecampane extract according to the present invention provides antibacterial activity equal to or better than that of conventionally used synthesized antibacterial agents.

EXAMPLE 4

Test of Antibacterial Activity in Cream Form

Antibacterial activity against *Staphylococcus aureus* (ATCC 6538P), *Escherichia coli* (ATCC 8739), *Pseudomonas aeruginosa* (ATCC 9027), *Candida albicans* (ATCC 10231) and *Aspergillus niger* (ATCC 9642) microbial strains were tested for the creams 1–4 with composition shown in the following Table 4. The test result is shown in Tables 4a–4e.

TABLE 4

| Components | Cream 1 | Cream 2 | Cream 3 | Cream 4 |
|---|---|---|---|---|
| Glycerin | 4.00 | 4.00 | 4.00 | 4.00 |
| Disodium EDTA | 0.02 | 0.02 | 0.02 | 0.02 |
| Methyl p-benzoate | — | — | 0.20 | — |
| Polyglyceryl 3-methyl glucose distearate | 2.50 | 2.50 | 2.50 | 2.50 |
| Glyceryl stearate/PEG-100 stearate | 1.00 | 1.00 | 1.00 | 1.00 |
| Glyceryl stearate | 1.00 | 1.00 | 1.00 | 1.00 |
| Cetearyl alcohol | 0.80 | 0.80 | 0.80 | 0.80 |
| Cholesteryl/behenyl/octyldodecyl lauroyl glutamate | 0.40 | 0.40 | 0.40 | 0.40 |
| Hydrogenated decyl olivate | 0.60 | 0.60 | 0.60 | 0.60 |
| Caprylic/capryic triglyceride | 4.00 | 4.00 | 4.00 | 4.00 |
| Squalane | 3.00 | 3.00 | 3.00 | 3.00 |
| Ethoxy diglycol olate | 2.00 | 2.00 | 2.00 | 2.00 |
| Mido formseed oil | 2.70 | 2.70 | 2.70 | 2.70 |
| Dimethicone | 0.50 | 0.50 | 0.50 | 0.50 |
| Cyclomethicone | 1.50 | 1.50 | 1.50 | 1.50 |
| Imidazolinyl urea | — | — | 0.30 | — |
| Polyacrylamide/C13–14 isoparaffin/laurece-7 | 1.20 | 1.20 | 1.20 | 1.20 |
| Water-soluble chitosan/elecampane extract (3:1) | 5.00 | 10.00 | — | — |
| Citric acid (10%) | — | — | 0.20 | 0.20 |

TABLE 4-continued

| Components | Cream 1 | Cream 2 | Cream 3 | Cream 4 |
|---|---|---|---|---|
| Potassium hydroxide (10%) | 0.50 | 0.50 | — | — |
| Compound fragrance | Proper quantity | Proper quantity | Proper quantity | Proper quantity |
| Pure water | Proper quantity | Proper quantity | Proper quantity | Proper quantity |

TABLE 4a

Antibacterial Activity against *Staphylococcus aureus*

| Item | Immediately after inoculation | After 1 hr | After 3 hr | After 5 hr | After 7 hr |
|---|---|---|---|---|---|
| Cream 1 | 1.19E+07 | 4.07E+04 | 1.10E+04 | 1.82E+04 | 4.68E+04 |
| Cream 2 | 1.19E+07 | 1.82E+04 | 7.59E+03 | 2.57E+03 | 1.40E+03 |
| Cream 3 | 1.19E+07 | 1.10E+04 | 5.50E+02 | <1.00E+01 | <1.00E+01 |
| Cream 4 | 1.19E+07 | 3.72E+06 | 2.82E+06 | 1.26E+06 | 1.70E+06 |

TABLE 4b

Antibacterial Activity against *Escherichia coli*

| Items | Immediately after inoculation | After 1 day | After 2 days | After 4 days | After 8 days | After 24 days |
|---|---|---|---|---|---|---|
| Cream 1 | 6.90E+06 | 3.63E+04 | 1.41E+04 | 7.59E+03 | 3.72E+02 | <1.00E+01 |
| Cream 2 | 6.90E+06 | 2.57E+02 | 2.40E+01 | <1.00E+01 | <1.00E+01 | <1.00E+01 |
| Cream 3 | 6.90E+06 | 5.50E+02 | 9.50E+01 | 3.10E+01 | <1.00E+01 | <1.00E+01 |
| Cream 4 | 6.90E+06 | 3.39E+05 | 7.59E+04 | 6.76E+04 | 1.82E+04 | 1.05E+05 |

TABLE 4c

Antibacterial Activity against *Pseudomonas aeruginosa*

| Items | Immediately after inoculation | After 1 hr | After 3 hr | After 5 hr | After 7 hr | After 14 hr |
|---|---|---|---|---|---|---|
| Cream 1 | 2.66E+05 | 2.63E+04 | 8.32E+02 | 1.32E+02 | 2.30E+01 | <1.00E+01 |
| Cream 2 | 2.66E+05 | 1.51E+04 | 1.62E+02 | 7.90E+01 | 1.45E+01 | <1.00E+01 |
| Cream 3 | 2.66E+05 | 8.32E+04 | 2.14E+03 | 9.12E+02 | 3.39E+02 | 4.70E+01 |
| Cream 4 | 2.66E+05 | 3.61E+05 | 2.57E+06 | 3.39E+05 | 2.24E+05 | 7.59E+06 |

TABLE 4d

Antibacterial Activity against *Candida albicans*

| Items | Immediately after inoculation | After 1 day | After 2 days | After 4 days | After 8 days | After 24 days |
|---|---|---|---|---|---|---|
| Cream 1 | 7.00E+06 | 2.09E+05 | 6.74E+04 | 3.80E+04 | 2.63E+04 | 1.45E+04 |
| Cream 2 | 7.00E+06 | <1.00E+03 | <1.00E+02 | <1.00E+01 | <1.00E+01 | <1.00E+01 |
| Cream 3 | 7.00E+06 | 4.17E+06 | 2.69E+06 | 8.13E+05 | 2.69E+05 | 2.35E+04 |
| Cream 4 | 7.00E+06 | 6.03E+06 | 6.52E+06 | 3.39E+06 | 2.63E+06 | 3.24E+06 |

TABLE 4e

Antibacterial Activity against *Aspergillus niger*

| Items | Immediately after inoculation | After 1 day | After 3 days | After 5 days | After 7 days | After 14 days |
|---|---|---|---|---|---|---|
| Cream 1 | 3.20E+06 | 1.40E+03 | 1.35E+03 | 1.00E+03 | 7.50E+02 | 3.70E+02 |
| Cream 2 | 3.20E+06 | 1.35E+03 | 1.11E+03 | 7.45E+02 | 5.50E+02 | 2.15E+02 |
| Cream 3 | 3.20E+06 | 1.00E+03 | 2.50E+02 | 1.75E+02 | 3.50E+01 | <1.00E+01 |
| Cream 4 | 3.20E+06 | 2.25E+04 | 1.50E+04 | 8.70E+03 | 5.40E+03 | 3.50E+03 |

Cream 2 containing effective amount of the natural cell control carrier of the present invention showed antibacterial activity comparable to that of cream 3, as in the milk lotions. Although cream and milk lotion are similar in constituents, their antiseptic effects may be different depending on physical properties. The above result shows that the natural cell control carrier comprising water-soluble chitosan-elecampane extract according to the present invention provides stable antibacterial activity regardless of its physical properties.

EXAMPLE 5

Patch Test Result

A closed patch test was performed for the cosmetic forms prepared in Examples 2–4. The result is shown in the following Table 5.

After applying a patch for 24 hr and then removing it, the tested area was observed after 1 hr and 24 hr. The presence and/or size of erythema were evaluated with weight. Average irritation indices (mean score) were calculated by dividing the total irritation scores by the number of subjects according to the standard of International Contact Dermatitis Research Group (ICDRG).

TABLE 5

Patch Test Result

| Test Materials | Average Irritation Index (mean score) |
|---|---|
| Skin Lotion | |
| 1 | 2.09 |
| 2 | 2.40 |
| 3 | 3.75 |
| 4 | 2.50 |
| Milk Lotion | |
| 1 | 0.32 |
| 2 | 0.40 |
| 3 | 1.25 |
| 4 | 0.42 |
| Cream | |
| 1 | 0.32 |
| 2 | 0.40 |
| 3 | 0.84 |
| 4 | 0.42 |

As shown in Table 5, the cosmetic forms containing the natural cell control carrier of the present invention (forms 1 & 2) showed slightly lower average irritation indices compared with those containing the conventional synthesized antibacterial agents. The skin lotion showed 30–40% lower average irritation index; milk lotion, about 60% lower; and cream, about 50% lower.

From the result, it is evident that the natural cell control carrier of the present invention provides superior antibacterial effect and significantly reduced skin irritation as well as anti-inflammatory effect compared with the conventional synthesized antibacterial agents.

EXAMPLE 6

Anti-Inflammatory Effect Test (Anti-Inflammation Assay)

The anti-inflammatory effect of the natural cell control carrier comprising 3:1 (wt/wt) water-soluble chitosan and elecampane extract according to the present invention was tested as follows. Twenty healthy male and female subjects with no experience of drug hypersensitivity or drug side effect were selected. Methyl nicotinate was used as an inflammation-inducing material. Test material 1 was the natural cell control carrier according to the present invention, and test material 2 was indometacin, which is known to have a superior anti-inflammatory effect. Firstly, the initial "a" value of the inner part of the upper arm was determined with a chromameter (Minolta, CR-300). Then, 1.0% aqueous solution of said composition and 0.1% indometacin aqueous solution were closely patched at the test part for 4 hr. After removing the patch, the test part was washed with pure water. After waiting for 1 hr for the temporary inflammation reaction to disappear, "a" value was measured again with the chromameter. After dropping 80 $\mu$L of methyl nicotinate diluted to 3 mM with pure water in a filter paper disk with 1 cm of diameter, it was applied to each test part for 1–2 min. After removing the filter paper disk, each test part was washed sufficiently with pure water. After 30 min, "a" value was measured with the chromameter. The anti-inflammatory effect of the natural cell control carrier according to the present invention, indometacin and methyl nicotinate was calculated from the "a" values. The result shows that the natural cell control carrier of the present invention provides considerably superior anti-inflammatory effect compared with indometacin.

TABLE 6

Anti-Inflammatory Effect Test Result

| Items | "a" Value (n = 20) | Anti-Inflammatory Effect (%) |
|---|---|---|
| Initial value | 5.69 | |
| After applying methyl nicotinate | 10.84 | |
| After treating with natural cell control carrier | 5.83 | 52.3 |
| After indometacin | 6.38 | 41.14 |

As explained above, the natural cell control carrier comprising water-soluble chitosan (HFP) and elecampane (Inula Helenium L.) extract according to the present invention complements the weakness of each constituent and provides superior antibacterial activity and anti-inflammatory effect. Therefore, it can be widely used in food, cosmetics and medicine.

What is claimed is:

1. An antibacterial composition comprising effective amounts of water-soluble chitosan having a molecular weight in the range of 100,000 to 300,000 and elecampane (*Inula Helenium L.*) root extract, wherein said extract is obtained via extraction with ethanol.

2. The antibacterial composition according to claim 1, comprising from 0.01 to 99.99 wt. % of the water-soluble chitosan and from 0.01 to 99.99 wt. % of the elecampane root extract.

3. The antibacterial composition according to claim 2, comprising from 50.00 to 90.00 wt. % of the water-soluble chitosan and from 10.00 to 50.00 wt. % of the elecampane root extract.

4. An anti-inflammatory composition comprising effective amounts of water-soluble chitosan having a molecular weight in the range of 100,000 to 300,000 and elecampane (Inula Helenium L.) root extract, wherein said extract is obtained via extraction with ethanol.

5. The anti-inflammatory composition according to claim 4, which comprises 0.01 to 99.99 wt. % of the water-soluble chitosan and from 0.01 to 99.99 wt. % of the elecampane root extract.

6. The anti-inflammatory composition according to claim 4, comprising from 50.00 to 90.00 wt. % of the water-soluble chitosan and from 10.00 to 50.00 wt. % of the elecampane root extract.

* * * * *